United States Patent [19]
Green

[11] Patent Number: 6,103,201
[45] Date of Patent: Aug. 15, 2000

[54] PROPELLER AIR FRESHENER

[76] Inventor: Dennis E. Green, 102 Falcon Hills Dr., Highlands Ranch, Colo. 80126

[21] Appl. No.: 08/506,545

[22] Filed: Jul. 25, 1995

[51] Int. Cl.$^7$ .................................................... A61L 9/12
[52] U.S. Cl. ............................ 422/124; 239/34; 239/289; D23/366
[58] Field of Search .................................. 422/120, 124; 239/34, 53, 54, 289; D23/366; 454/157, 328, 329; 416/62, 146 R

[56] References Cited

U.S. PATENT DOCUMENTS

| | | | |
|---|---|---|---|
| 712,177 | 10/1902 | Bradshaw | 416/146 R |
| 725,086 | 4/1903 | Jacobs | 416/146 R |
| 1,066,851 | 7/1913 | Siefert | 416/146 R |
| 1,274,649 | 8/1918 | Wilson | 454/329 |
| 1,743,994 | 1/1930 | Waterbury | 454/329 |
| 2,720,013 | 10/1955 | Clarke | 416/62 |
| 2,779,624 | 1/1957 | Friedman | 239/54 |
| 2,972,941 | 2/1961 | Bennett | 454/329 |
| 3,099,201 | 7/1963 | Gottlieb | 454/329 |
| 4,523,870 | 6/1985 | Spector | 454/157 |
| 4,802,626 | 2/1989 | Forbes et al. | 239/54 |
| 4,813,344 | 3/1989 | Grief | 454/157 |
| 4,840,773 | 6/1989 | Wade | 422/124 |
| 4,876,070 | 10/1989 | Tsukahara et al. | 422/122 |
| 4,944,898 | 7/1990 | Glaser | 239/34 |
| 5,141,707 | 8/1992 | Brite | 422/124 |
| 5,170,938 | 12/1992 | Dewing | 239/52 |
| 5,269,723 | 12/1993 | Bender | 422/124 |
| 5,368,822 | 11/1994 | McNeil | 422/124 |
| 5,383,765 | 1/1995 | Baxter et al. | 422/124 |
| 5,407,642 | 4/1995 | Lord | 422/120 |
| 5,422,078 | 6/1995 | Colon | 239/54 |

*Primary Examiner*—Elizabeth McKane
*Attorney, Agent, or Firm*—Dorr, Carson, Sloan & Birney, P.C.

[57] ABSTRACT

An air freshener employs a rotor made of a scent-bearing material to disperse a fragrance in the air flowing from a vent, for example, in a vehicle. The rotor can be molded from scented plastic (e.g., low-density polyethylene impregnated with a fragrance). The rotor is rotatably mounted to a base having a clip or fastener that can be attached to the louvers covering the vent. The air flow through the vent causes the rotor to rotate and thereby disperses the scent. The base can also be made of a scent-bearing material. For example, the rotor can be shaped like an aircraft propeller, pinwheel, or ventilation fan. If an aircraft propeller is used, the base can take the appearance of an aircraft engine cowling. The rotor can also be generally disk-shaped bearing an arbitrary design (e.g., a flower, character, or company logo). A series of openings direct air flow through the rotor disk and over corresponding airfoil surfaces to cause the rotor to spin.

21 Claims, 3 Drawing Sheets

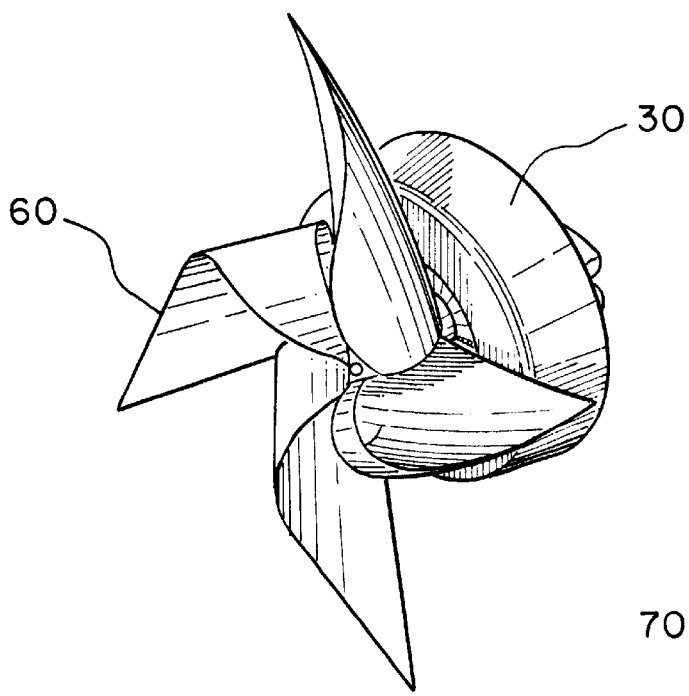
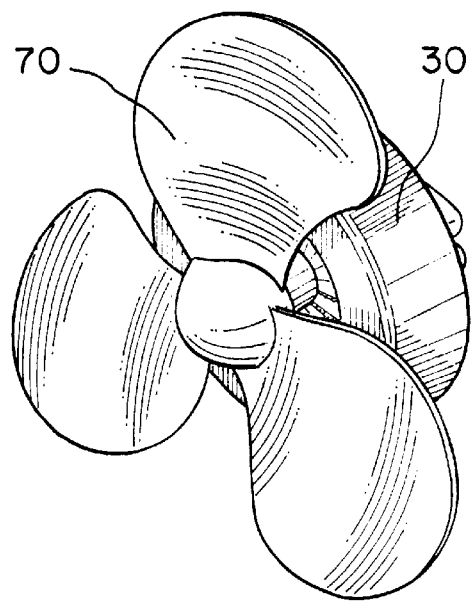
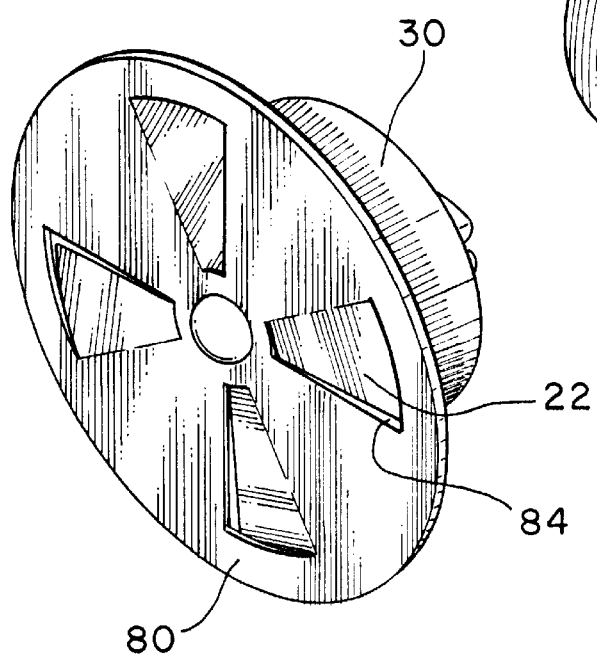

PROPELLER AIR FRESHENER

BACKGROUND OF THE INVENTION

1. Field of the Invention

The present invention relates generally to the field of air fresheners. More specifically, the present invention discloses a propeller air freshener for use primarily in vehicles.

2. Statement of the Problem

Air fresheners have been used for many years in many settings, including cars and other types of motor vehicles. Most air fresheners employ a separate reservoir containing a liquid fragrance or a replaceable scent cartridge (e.g., a scent disk, block, or wafer) within the air freshener housing. Such designs require a separate container or dispenser into which the scent reservoir is added. This increases the initial cost of manufacturing the air freshener due to the extensive assembly and packaging required to preserve the scent until the air freshener has been placed in service by the customer. In addition, it is difficult to profitably market refills or replacement scent cartridges. Many retailers do not want to carry the inventory or take up shelf space for refills. This makes it very difficult to compete with the inexpensive disposable air fresheners that are often sold for less than one dollar each.

A number of very inexpensive air fresheners have also been marketed in the past, primarily for use in cars and other motor vehicles. These devices often have the form of small three-dimensional cloth figures (e.g., a skunk) that have been impregnated with a fragrance. Other air fresheners use a variety of two-dimensional shapes. The scent from these devices tends to be overpowering for an initial period after the device is unpackaged, but then the scent dissipates after a relatively short period of exposure. The relatively short life of such air fresheners is due to the fact that no attempt is made to control dissipation of the scent. The scent continually evaporates regardless of whether the vehicle is occupied or the vehicle's ventilation system is in use.

Examples of prior art in the field of air fresheners include the following:

| Inventor | U.S. Pat. No. | Issue Date |
| --- | --- | --- |
| McNeil | 5,368,822 | Nov. 29, 1994 |
| Bender | 5,269,723 | Dec. 14, 1993 |
| Tsukahara et al. | 4,876,070 | Oct. 24, 1989 |
| Wade | 4,840,773 | June 20, 1989 |
| Dawn | 4,808,347 | Feb. 28, 1989 |

McNeil shows a scent-dispensing device having a front face with vents and a rear support for securing the housing to the vent of a blower (e.g., a furnace or air conditioner). A fragrance block with passages therethrough is inserted into the housing.

Bender shows an example of an air freshener for use in vehicles.

Tsukahara et al. disclose an air blower apparatus having synthetic resin components that come in contact with the air flow. The synthetic resin components are molded from polypropylene containing an antimicrobial agent.

Wade shows an air freshener with a U-shaped clip 54 that is used to fastened the air freshener to the louvers covering the interior vent in an automobile.

Dawn shows a fan-driven air freshener that is designed to be plugged into the cigarette lighter of a vehicle. The fan propeller 29 draws air through a replaceable scent disk 39 as shown in FIGS. 4 and 5 of the Dawn patent.

In addition to the prior art listed above, scented plastics have been used for many years in a variety of fields, including air fresheners. For example, low-density polyethylene can be impregnated with fragrance during the molding process, so that the fragrance material makes up approximately 20% to 25% of the molded article. Scented plastics have conventionally been used as replaceable scent cartridges (e.g., disks, blocks, or wafers) within the air freshener housing, rather than as the air freshener device itself. Here again, this approach requires a separate container or dispenser into which a scent disk or scent block is added to provide a fragrance reservoir.

3. Solution to the Problem

None of the prior art references uncovered in the search show an air freshener that uses a rotor or propeller made of scented plastic to disperse a fragrance in the air flow from a vent. In particular, the present invention eliminates the need for a separate air freshener structure and fragrance reservoir, by combining scented plastic directly into the air freshener structure. In addition, the rotor spins to dispense the fragrance only when the vehicle's ventilation system is in operation. This helps to lengthen the useful life of the air freshener by dispensing the scent only when the vehicle is in operation. The present device can be easily molded and assembled at minimal cost so that it can compete with even the least expensive air fresheners on the market. Finally, the present invention has considerable play value, which is useful in keeping children (or adults) entertained and amused.

SUMMARY OF THE INVENTION

This invention provides an air freshener that employs a rotor made of a scent-bearing material to disperse a fragrance in the air flowing from a vent, for example, in a vehicle. The rotor can be molded from scented plastic (e.g., low-density polyethylene that has been impregnated with a fragrance). The rotor is rotatably mounted to a base having a clip or fastener that can be attached to the louvers covering the vent. The air flow through the vent causes the rotor to rotate and thereby disperses the scent. The base can also be made of a scent-bearing material. For example, the rotor can be shaped like an aircraft propeller, pinwheel, or ventilation fan. If an aircraft propeller is used, the base can take the appearance of an aircraft engine cowling. The rotor can also be generally disk-shaped bearing an arbitrary design (e.g., a flower, character, or company logo). A series of openings direct air flow through the rotor disk and over corresponding airfoil surfaces to cause the rotor to spin.

A primary object of the present invention is to provide an air freshener in which the fragrance is an integral part of the structure and does not require a separate reservoir or refill for the fragrance.

Another object of the present invention is to provide an air freshener that is entertaining and fun.

Yet another object of the present invention is to provide a disposable air freshener that is inexpensive to manufacture and assemble.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 6 is a front perspective view of an alternative embodiment in which the rotor 60 is shaped like a pinwheel.

FIG. 7 is a front perspective view of an alternative embodiment in which the rotor 70 is shaped like the blades of a ventilation fan.

FIG. 8 is a front perspective view of another alternative embodiment in which the rotor 80 is generally disk-shaped with a number of openings 84 for directing air flow over the airfoil surfaces 22 to spin the rotor.

DETAILED DESCRIPTION OF THE INVENTION

Figure 1:
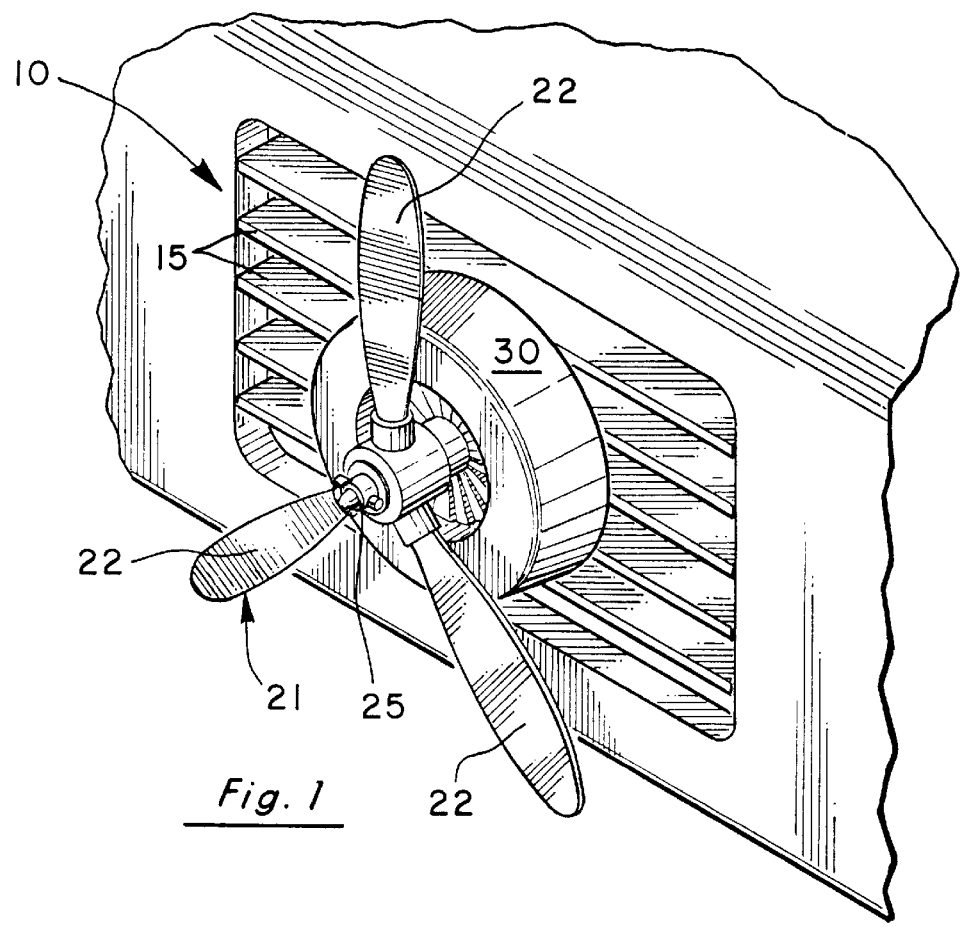
FIG. 1 is a front perspective view of the air freshener attached to the interior vent 10 of a car.

Turning to FIG. 1, a front perspective view is provided showing the air freshener attached to the interior vent 10 of an automobile. Air flows through the vent 10 and into the interior of the vehicle as a result of either the vehicle's ventilation fan or the vehicle's velocity along the highway. The vent 10 is normally equipped with a series of louvers 15 that allow the air flow to be directed in a desired direction within the vehicle. The louvers 15 usually extend parallel to one another in either a horizontal or vertical orientation.

Figure 2:
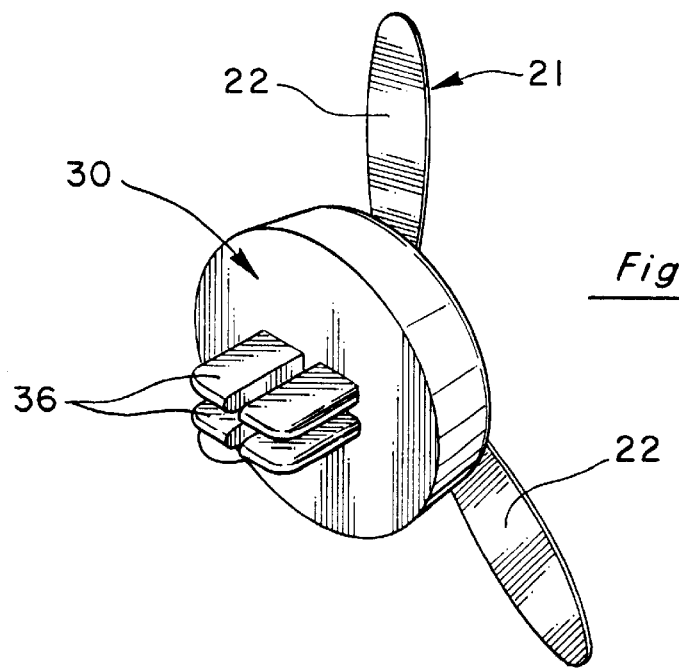
FIG. 2 is a rear perspective view of the air freshener corresponding to FIG. 1.

FIG. 2 is a corresponding rear perspective view of the air freshener. The air freshener generally consists of a rotor 21 made of a scent-bearing material, such as low-density polyethylene impregnated with a fragrance. The rotor can be molded in one piece using conventional molding technology for making scented plastics. The rotor 21 includes a series of airfoil surfaces 22 that cause the rotor to rotate when it is placed in an air flow. These airfoil surfaces 22 can be curved surfaces such as those commonly found on propeller blades. However, it is not necessary to actually generate aerodynamic lift in the present invention, so an angled surface would be sufficient to cause the rotor to spin.

Figure 3:
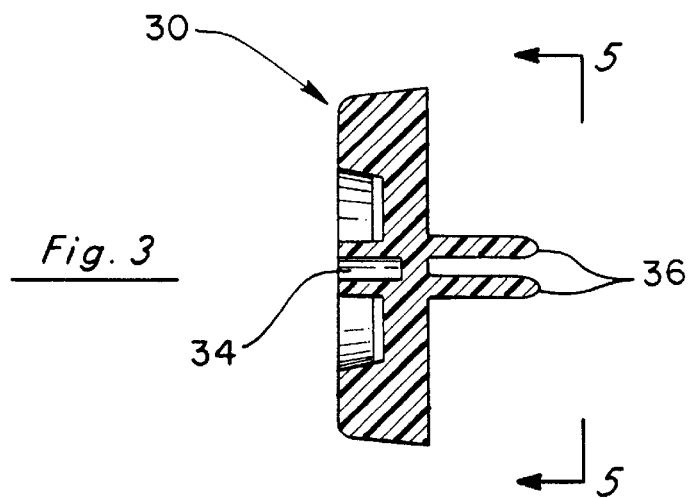
FIG. 3 is a cross-sectional view of the engine cowling base 30 corresponding to FIG. 1.
Figure 4:
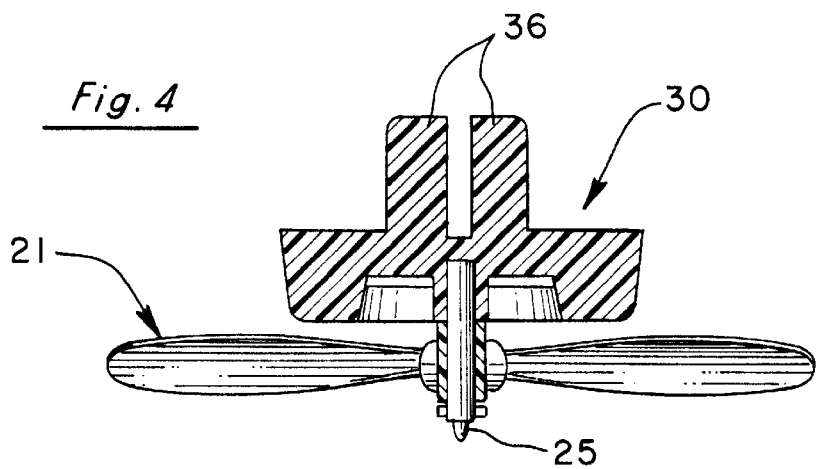
FIG. 4 is cross-sectional view of the engine cowling base 30, propeller 21, and shaft 25 used to attach the propeller to the base, corresponding to FIG. 1.

The rotor 21 is rotatably attached to a base 30 as shown in FIGS. 1 and 4. In the one embodiment, the rotor 21 has the general appearance of an aircraft propeller and the base 30 resembles the front portion of an aircraft engine cowling. A corresponding cross-sectional view of the engine cowling base is depicted in FIG. 3. FIG. 4 is cross-sectional view of the base 30, rotor 21, and shaft 25 used to attach the rotor to the engine cowling base 30. As shown in FIG. 4, the shaft 25 passes through a hole in the center of the rotor 21 so that the rotor 21 can spin freely about the shaft 25. The end of the shaft is press-fit into a socket 34 in the base 30. Thus, the shaft 25 is fixed relative to the base, but allows the rotor 21 to freely rotate on the shaft. Alternatively, the rotor 21 and shaft 25 can be molded as a single piece that can rotate freely with respect to the base 30.

The base 30 can also be made of a scent-bearing material, such as scented plastic. This allows the use of a plurality of scents or colors. For example, the base 30 can be one fragrance, e.g., strawberry, and the rotor can be another fragrance, e.g., banana. Other possible scent combinations include chocolate/raspberry or raspberry/lemonade. These types of combinations are very novel and add complexity to fragrances that cannot be directly mixed because of dilution. The present invention permits such combinations because the fragrances only become mixed in the air stream. Various combinations of materials, colors, textures, and scented and unscented components can also be used to enhance the aesthetic appeal and entertainment value of the device. Different scented or unscented materials could be used for the rotor 21, base 30, shaft 25, and clip 36. For example, the base 30 could made of scented plastic while the rotor 21 is made of unscented material. The fragrance from the base 30 would be picked up by the passing air stream and dispersed by the rotor 21.

Figure 5:
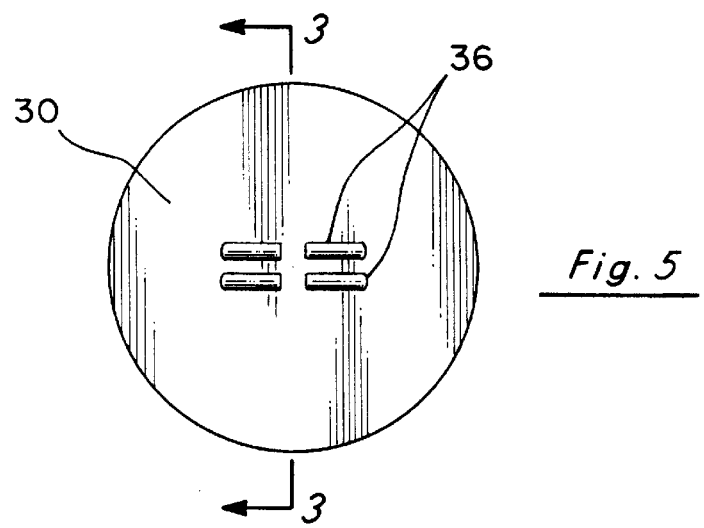
FIG. 5 is a rear view of the engine cowling base 30 showing the clip 36 used to the attach the air freshener assembly to the vent louvers, corresponding to FIG. 1.

FIG. 5 is a rear view of the base 30 showing one embodiment of the clip 36 used to the attach the air freshener to the louvers 15 of the vent 10. The clip 36 consists of at least two parallel prongs extending rearward from the rear surface of the base 30. The spacing between the prongs of the clip 36 is selected to allow the prongs to grip opposing sides of one of the louvers 15. The embodiment illustrated in FIG. 5 consists of four prongs arranged in a two-by-two grid with a vertically-oriented separation and a horizontally-oriented separation between each pair of prongs to accommodate both vertical and horizontal louvers. This also creates several alternative means for attaching the air freshener to the vent 10. The vertically-oriented and horizontally-oriented separations provide two different spacings between the prongs (e.g., approximately 0.15–0.2 inch and approximately 0.1 inch, respectively) to accommodate louvers 15 of different thicknesses. Alternatively, the clip 36 can be inserted in the space between two adjacent louvers so that the outward-facing edges of the prongs engage the louvers 15. The base could also be attached to the vent by other means, such as an adhesive pad, Velcro, etc.

The first embodiment depicted in FIGS. 1 through 5 shows a rotor 21 having the general appearance of an aircraft propeller. Three alternative embodiments of the rotor are illustrated in FIGS. 6 through 8. FIG. 6 is a front perspective view of an alternative embodiment in which the rotor is generally shaped like a pinwheel 60. FIG. 7 shows a rotor having the shape of a ventilation fan 70. The rotor could also be shaped like a boat propeller, turbine vanes, paddle wheel, etc.

FIG. 8 illustrates a disk-shaped rotor 80 with a series of openings 84 that direct the air flow through the rotor disk and over corresponding airfoil surfaces 22 to cause the disk to spin. Other than the openings 84 and airfoil surfaces, the face of the rotor 21 in FIG. 8 presents a generally flat surface that can be decorated with an attractive design, geometric patterns, licensed characters, company logos, etc. Other equivalent configurations for the rotor could be readily substituted. For example, the rotor could be disguised as a daisy or a sunflower with the peripheral petals acting as the airfoil surfaces to cause rotation. The rotor could take the form of a bird, butterfly, or bee with its wings spread. The rotor could also be designed as a merry-go-round with a series of slots to direct the air flow through the rotor disk over a corresponding set of air foils.

The preceding discussion has assumed that the present invention would be used primarily in an automobile or motor vehicle. It should be expressly understood that the present invention is readily adaptable for use in other settings. For example, the air freshener can be attached to the vent of a forced-air heating system, air conditioner, or HVAC system in a building. The device could also be attached to the grill of a conventional ventilation fan, air filter, or humidifier.

The above disclosure sets forth a number of embodiments of the present invention. Other arrangements or embodiments, not precisely set forth, could be practiced under the teachings of the present invention and as set forth in the following claims.

I claim:

1. An air freshener primarily for use with a vent supplying a flow of air, said air freshener comprising:

a base;

a rotor made of a scent-bearing material rotatably attached to said base, said rotor having a plurality of airfoil surfaces causing rotation of said rotor in an air flow; and means for attaching said base to a vent to permit rotation of said rotor in said flow of air from said vent to disperse said scent.

2. The air freshener of claim 1 wherein said rotor is a propeller.

3. The air freshener of claim 1 wherein said rotor is a pinwheel.

4. The air freshener of claim 1 wherein said rotor has the shape of ventilation fan blades.

5. The air freshener of claim 1 wherein said rotor comprises a disk having a plurality of openings for directing said air flow over said airfoil surfaces.

6. The air freshener of claim 1 wherein said base is comprised of scent-bearing material.

7. The air freshener of claim 1 wherein said vent includes at least one louver, and wherein said means for attaching said base comprises a clip for removably engaging said louver.

8. The air freshener of claim 7 wherein said clip comprises a plurality of flexible prongs extending from said base and being spaced apart from one another to removably engage said louver.

9. An air freshener primarily for use with a vent for supplying a flow of air, said air freshener comprising:

a base;

a propeller rotatably attached to said base, said propeller being made of a scent-bearing material; and means for attaching said base to a vent to permit said propeller to rotate in said flow of air and disperse said scent.

10. The air freshener of claim 9 wherein said scent-bearing material comprises polyethylene impregnated with a fragrance.

11. The air freshener of claim 9 wherein said vent includes at least one louver, and wherein said means for attaching said base comprises a clip for removably engaging said louver.

12. The air freshener of claim 11 wherein said clip comprises a plurality of flexible prongs extending from said base and being spaced apart from one another to removably engage said louver.

13. The air freshener of claim 9 wherein said base has the shape of an aircraft engine cowling.

14. The air freshener of claim 9 wherein said base is comprised of scent-bearing material.

15. An air freshener primarily for use in vehicles having a vent with louvers for supplying a flow of air to the interior of said vehicle, said air freshener comprising:

a base made of a scent-bearing material;

a rotor rotatably attached to said base, said rotor being made of a scent-bearing material; and a clip extending from said base for removably attaching said base to a louver to permit said rotor to rotate in said flow of air and disperse said scent.

16. The air freshener of claim 15, wherein said scent-bearing material comprises polyethylene impregnated with a fragrance.

17. The air freshener of claim 15, wherein said clip comprises a plurality of flexible prongs extending from said base and being spaced apart from one another to removably engage at least one of said louvers.

18. The air freshener of claim 15 wherein said base has the shape of an aircraft engine cowling.

19. The air freshener of claim 15 wherein said propeller has the shape of an aircraft propeller.

20. The air freshener of claim 15 wherein said propeller is a pinwheel.

21. The air freshener of claim 15 wherein said propeller has the shape of ventilation fan.

* * * * *

UNITED STATES PATENT AND TRADEMARK OFFICE
CERTIFICATE OF CORRECTION

PATENT NO.    : 6,103,201
DATED         : August 15, 2000
INVENTOR(S)   : Green

It is certified that error appears in the above-identified patent and that said Letters Patent is hereby corrected as shown below:

<u>Title page,</u>
Insert -- [*] Notice: Under 35 U.S.C. 154(b), the term of this patent shall be extended for 587 days. --.

Signed and Sealed this

Eleventh Day of February, 2003

JAMES E. ROGAN
*Director of the United States Patent and Trademark Office*